United States Patent [19]
Chu

[11] 3,956,224
[45] May 11, 1976

[54] PREPARATION OF POWDERED CROSSLINKED POLYALKYLENE OXIDES

[75] Inventor: Nan S. Chu, Hartsdale, N.Y.

[73] Assignee: Union Carbide Corporation, New York, N.Y.

[22] Filed: June 29, 1973

[21] Appl. No.: 375,147

Related U.S. Application Data

[63] Continuation-in-part of Ser. No. 160,133, July 7, 1971, abandoned.

[52] U.S. Cl. ............... 260/33.6 R; 260/33.4 R; 260/33.6 UA; 260/33.8 R; 260/33.8 UA; 260/901
[51] Int. Cl.²................................. C08K 5/01
[58] Field of Search........... 260/901, 2 A, 33.6 R, 260/33.6 EP, 33.6 UA, 33.4 R, 33.8 R, 33.8 UA

[56] References Cited
UNITED STATES PATENTS

| | | | |
|---|---|---|---|
| 3,498,933 | 3/1970 | Fey | 260/2 A |
| 3,579,611 | 5/1971 | Holub et al. | 260/901 |

FOREIGN PATENTS OR APPLICATIONS

| | | | |
|---|---|---|---|
| 1,595,806 | 6/1970 | France | 260/901 |
| 756,190 | 4/1967 | Canada | 260/901 |

OTHER PUBLICATIONS

Davidson et al., "Water Soluble Resins," Second Edition, pp. 197–199, Reinhold Book Corp., New York.

*Primary Examiner*—Murray Tillman
*Assistant Examiner*—J. Ziegler
*Attorney, Agent, or Firm*—J. Hart Evans

[57] ABSTRACT

A process for producing powdered chemically crosslinked poly(alkylene oxide) of molecular weight of at least 100,000 which comprises contacting poly(alkylene oxide) with a suitable crosslinking agent in the presence of a free radical catalyst, and a liquid medium containing a solvent-nonsolvent mixture for said poly(alkylene oxide) wherein the non-solvent portion constitutes at least 35% and up to 100% by weight of the liquid medium, at a temperature and for a time sufficient to crosslink said poly(alkylene oxide).

14 Claims, No Drawings

PREPARATION OF POWDERED CROSSLINKED POLYALKYLENE OXIDES

This application is a continuation-in-part of co-pending application Ser. No. 160,133 filed July 7, 1971, now abandoned.

This invention relates to chemically cross-linked poly(alkylene oxide) and more particularly to a process for producing "powdered" cross-linked poly(alkylene oxide).

It is known that poly(alkylene oxide) such as poly(ethylene oxide) can be cross-linked readily through irradiation with gamma rays. Poly(ethylene oxide) has been shown to form a cross-linked polymer of varying properties through irradiation with gamma rays such as those emitted by a cobalt 60 source. The properties of these irradiated poly(ethylene oxides) are highly dependent on the irradiation dose, that is, the irradiated poly(ethylene oxide) may range in properties from a soluble polymer with properties similar to the unirradiated polymer, to a highly cross-linked horny solid, insoluble in any solvent. Unfortunately, gamma radiation involves the use of a potentially dangerous source with costly protective measures involved in its use, and therefore, this route is not the most desirable process for cross-linking poly(ethylene oxides).

In order to eliminate some of the disadvantages of obtaining cross-linked poly(alkylene oxide), via irradiation, it has been proposed to chemically cross-link poly(alkylene oxide) utilizing a di-vinyl monomer in the presence of a free radical catalyst (Canadian Pat. No. 756,190).

Unfortunately, however, this known chemical technique is not entirely satisfactory from a practical commercial standpoint, because the highest degree of cross-linking is obtained by employment of poly(alkylene oxide) in molten form. The utilization of poly(alkylene oxide) in molten form is difficult to process, whereas high concentrations of poly(alkylene oxide) in solution are extremely viscous and consequently also difficult to handle.

In my co-pending application Ser. No. 160,134 filed concurrently herewith, now U.S. Pat. No. 3,734,876 I described a process for preparing cross-linked poly(alkylene oxide) which involves a rather simple chemical reaction and does not require a source of gamma radiation. Moreover, according to the process described therein, it was found that by employment of a select class of cross-linking agents and by utilization of a solvent during cross-linking that the poly(alkylene oxide) starting material could be employed as a dilute solution without the necessity of resorting to melting the poly(alkylene oxide) prior to reaction in order to obtain highly cross-linked products. Thus, many of the problems incident to prior art techniques were resolved.

The cross-linked poly(alkylene oxide) product obtained by the process described in my co-pending application is generally in the form of a gel. For many important commercial applications, this presents little or no problems. On the other hand, there are commercial applications wherein it is desired that the product be obtained in the form of a "powdery" material.

The term "powdery" or "powdered" material as used herein means a free flowing powder which is free from agglomeration.

Accordingly, in a broad aspect, the present invention contemplates the production of powdery cross-linked poly(alkylene oxide) by a process which comprises contacting poly(alkylene oxide) with a cross-linking agent, as hereinafter defined, in the presence of a free radical catalyst and a liquid medium containing a solvent-nonsolvent mixture for the poly(alkylene oxide) and wherein the nonsolvent portion constitutes at least 35% and up to 100% of the weight of the liquid medium.

In a more specific aspect, the present invention contemplates a process for producing powdered cross-linked poly(ethylene oxide) having a molecular weight of at least 100,000 which comprises contacting poly(ethylene oxide) with a cross-linking agent represented by the formula:

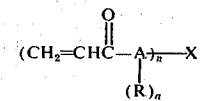

wherein A is nitrogen or oxygen; n has a value of 2 or more, R is hydrogen, an alkyl of 1–6 carbon atoms or aryl of 6 to 14 carbon atoms; X can be a substituted or unsubstituted polyvalent residue of an organic compound, such as —$C_yH_{2y}$— wherein y is an integer of 1 to 50, —$C_xH_{2x}(OC_xH_{2x})_m$— wherein x is an integer of 2 to 4 and m is an integer of 1 to 1000 or more; polyvalent cycloalkyl of 5 to 7 ring carbon atoms; polyvalent arylene of 6 to 14 ring carbon atoms

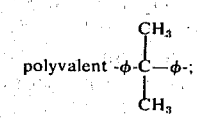

di or trivalent glyceryl; trimethylol propane; the divalent, trivalent and tetravalent residues of pentaerythritol; the polyvalent residues of the epoxidized fatty acid glycerides and the divalent, trivalent or higher polyvalent residues of the carbohydrates such as glucose, sucrose, sorbitol and the like; with the proviso that when A is oxygen, a is o and when A is nitrogen, a is 1; in the presence of a free radical catalyst, preferably aliphatic diacyl peroxides and a liquid medium containing a solvent-nonsolvent mixture for the poly(ethylene oxide) wherein the nonsolvent portion constitutes at least about 35% and up to 100% by weight of the liquid medium, preferably 40% to about 80% by weight of the liquid medium.

Advantageously, the manner of mixing the reactants is not critical and the mixing can be effected by a variety of conventional techniques. For example, the poly(ethylene oxide) reactant can be first added to the liquid medium followed by the addition of the cross-linking agent and the free radical catalyst. Alternatively, the reactants may be introduced simultaneously to the reaction vessel containing the liquid medium.

The poly(alkylene oxide) which can be chemically cross-linked according to this invention includes a wide variety of known poly(alkylene oxides). It is believed that any poly(alkylene oxide) with a hydrogen atom on the carbon atom adjacent to the ether oxygen can be cross-linked as disclosed herein. Among the poly(alkylene oxides) which can be cross-linked according to this invention include homopolymers of ethylene oxide, propylene oxide and butylene oxide, copolymers of ethylene oxide, propylene oxide, butylene oxide and mixtures thereof. In general, poly(alkylene oxides) having an average molecular weight of at least 100,000 to about 5,000,000 or greater, up to 10,000,000, are operable. This invention is particularly adapted to the chemical cross-linking of poly(ethylene oxide) having a molecular weight of at least 100,000 or a copolymer of poly(alkylene oxide) containing more than 90 percent by weight of ethylene oxide, which results in cross-linked products having a high degree of water absorption qualities, but is in no way, restricted thereto.

Advantageously, the poly(alkylene oxide) starting material can be in "powdered" form and according to the novel method of the invention, this form is maintained throughout the invention method for producing the powdered poly(alkylene oxide).

The cross-linking agents which are suitable in the practice of this invention can be represented by the general formula:

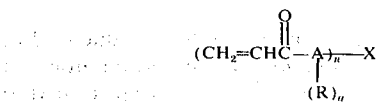

wherein A is nitrogen or oxygen; n has a value of 2 or more, R is hydrogen, an alkyl of 1–6 carbon atoms or aryl of 6 to 14 carbon atoms; X can be a substituted or unsubstituted polyvalent residue of an organic compound, such as —$C_yH_{2y}$— wherein y is an integer of 1 to 50, —$C_xH_{2x}(OC_xH_{2x})_m$— wherein x is an integer of 2 to 4 and m is an integer of 1 to 1000 or more; -polyvalent cycloalkyl of 5 to 7 ring carbon atoms; -polyvalent arylene of 6 to 14 ring carbon atoms;

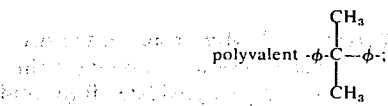

di or trivalent glyceryl; trimethylol propane; the divalent, trivalent and tetravalent residues of pentaerythritol; the polyvalent residues of the epoxidized fatty acid glycerides; and the divalent, trivalent or higher polyvalent residues of the carbohydrates such as glucose, sucrose, sorbitol and the like; with the proviso that when A is oxygen, a to 0 and when A is nitrogen, a is 1.

Merely as illustrative, compounds containing the above structure include 1,3-butylene glycol diacrylate, methylene bis-acrylamide, 1,4-butylene glycol diacrylate, 1,10-decanediol diacrylate, 1,6-hexamethylene diacrylate, neopentyl glycol diacrylate, 1,4-cyclohexyl diacrylate, p-xylene diacrylate, bis-phenol A diacrylate, tetraethylene glycol diacrylate, polyethylene glycol diacrylate, 2,2-dibromoneopentyl glycol diacrylate, 2,3-dibromo-2-butene-1,4-diol diacrylate, glycerol triacrylate, 1,1,1-trimethylol propane triacrylate, pentaerythritol triacrylate, pentaerythritol tetraacrylate, linseed oil epoxide acrylate, soybean oil epoxide acrylate and the various di-, tri- or polyacrylates of glucose, sucrose, sorbitol, 1,6-hexamethylene-bisacrylamide, 1,9-nonanediol diacrylate, 1,2,6-hexanetriol diacrylate, 1,2,6-hexanetriol triacrylate, 2,2-dimethyl propanediol diacrylate, 1,3-propanediol diacrylate, tetraethylene glycol diacrylate, trimethylolpropane polyoxyethylene 1000 triacrylate, 2,2,4-trimethyl-1,3-pentanediol diacrylate, 1,3-cyclopentyl diacrylate, 1,4-cycloheptyl diacrylate, cyclohexanpentol diacrylate, cyclohexanpentol triacrylate, cyclohexanpentol tetraacrylate, cyclohexanpentol penta-acrylate 4-methylresorcinol diacrylate, 1,8-dihydroxy anthracene diacrylate, 1,5-dihydroxy anthracene diacrylate, pyrocatechin diacrylate, resorcinol diacrylate, hydroquinone diacrylate, 4,4'-dihydroxydiphenyl diacrylate, pyrogallol triacrylate, pyrogallol diacrylate, epoxidized linseed oil diacrylate, epoxidized linseed oil triacrylate, epoxidized cottonseed oil triacrylate, epoxidized cottonseed oil pentaacrylate, epoxidized corn oil triacrylate, epoxidized and soybean oil tetraacrylate.

The amount of cross-linking agent required in the process of this invention depends, in part, on the molecular weight of the poly(alkylene oxide) and the efficiency of the cross-linking agent. It has been found that the higher the molecular weight and the more effective the cross-linking agent, the lesser the amount of cross-linking agent is required to obtain cross-linking, as indicated by the insolubility of the resultant polymer. In general, the amount of cross-linking agent required will represent from about 0.1 to about 12 weight per cent based on the weight of poly(alkylene oxide) employed and more preferably an amount within the range of from about 0.3 to about 10 percent. Ideally, if a polymer is completely cross-linked to an infinite network, i.e., only a single molecule exits, then the polymer will be insoluble in water. Different degrees of cross-linking can be measured roughly by the amount of swelling or absorption in a good solvent for the cross-linked polymer. In the present invention, cross-linking is determined by the ability to absorb water without dissolving in the water. The above range will give an end product with the best compromise of per cent of cross-linked poly(ethylene oxide) content (water insoluble but swellable fraction) and water pick-up ability (swellability) required when used in applications such as babies' diapers. However, it should be noted that concentrations outside the above range can also be used when products with either lower cross-linked poly(ethylene oxide) content, but higher swellability or with higher cross-linked poly(ethylene oxide) content, but lower swellability are desired.

A number of different free radical catalysts can be used in the process of this invention. Typical free radical catalysts include azobisisobutyronitrile, azobisbutyronitrile, benzoyl peroxide, acetyl peroxide, 2,4-dichlorobenzoyl peroxide, 2,2-azobis(2-methylpropionitrile) lauroyl peroxide, decanoyl peroxide, pelargonyl peroxide, and, in general, any free radical generating compound which will generate a substantial number of free radicals over a temperature range of interest from about 50°C. to about 100°C. The preferred free radical catalysts for poly(ethylene oxide) are aliphatic diacyl peroxides. The amount of catalyst can vary from 0.03 to about 3 per cent based on the weight of the poly(alkylene oxide) more preferably within the range of about 0.05 to 2 per cent. Again the preferred aliphatic diacyl peroxides can also be used in concentrations outside the above cited limits, but the product obtained would have a higher content of uncross-linked poly(ethylene oxide).

The temperature and the time of the reaction depend upon the individual peroxide used. For certain peroxides, the higher the reaction temperature used, the shorter the reaction time required. Thus, for example when acetyl peroxide is used at 80°–95°C., the preferred reaction time is 15–20 minutes. Prolonged heating may cause degradation of the product to such an extent that the cross-linked polymer becomes again soluble. It has been found that one can still obtain acceptable powdery cross-linked poly(ethylene oxide) provided adequate stirring is used even when the polymer mixture is heated at a temperature (89°–90°C.) well above its melting point for 20 minutes. As a general rule, therefore, the temperature for the reaction can be varied within the range of from about 50°C. to about 100°C. the preferred range being from about 60°C. to about 80°C.

An important criterion for the successful practice of the invention is the employment of a liquid medium containing a solvent-nonsolvent mixture for the reactants. As a general rule, any solvent which is capable of dissolving or highly swelling the poly(alkylene oxide) reactant at the prescribed reaction temperatures, and which is chemically inert to the various components of the reaction mixture can be used as the solvent portion of the liquid medium. Suitable solvents include, for example, methanol, benzene, methylene dichloride, ethylene dichloride and toluene. Likewise, the nonsolvent portion must be chemically inert to the components of the reaction mixture and must naturally be incapable of dissolving or swelling significant amounts of the poly(alkylene oxide) reactant under the reaction conditions. Suitable nonsolvents include aliphatic and cyclic hydrocarbons, such as, cyclohexane, cycloheptane, heptane, hexane, nonane, and kerosene. It has been found that powdery cross-linked polyalkylene oxide can be obtained according to the process when the nonsolvent component used in the liquid medium is at least 35% and up to 100% by weight of the weight of the liquid medium preferably from about 40 to about 80% by weight. The total product i.e., the liquid medium containing the solvent-nonsolvent mixture must not be capable of dissolving significant amounts of poly(alkylene oxide). In other words, the poly(alkylene oxide) must not be soluble, to any appreciable degree in the liquid medium. The amount of liquid medium employed generally is based on the amount of polyalkylene oxide to be crosslinked. As a general rule, there can be employed from about 2 parts to about 40 parts liquid medium per part poly(alkylene oxide) by weight. Preferably about 3 to 10 parts by weight liquid medium per part poly(alkylene oxide) by weight can be employed. However, we have found that no advantages have been obtained by the use of such high ratios.

The following Examples illustrate the preparation of powdery cross-linked poly(ethylene oxide).

EXAMPLE 1

Into a pressure bottle, benzene (38 ml), hexane (50 ml), 7.5 g of poly(ethylene oxide) (molecular wt. ~4 × $10^6$), 0.24 g. of poly(ethylene glycol) (200) diacrylate (in 4 ml benzene) and 0.8 ml of an acetyl peroxide solution were added after the bottle had been thoroughly flushed with nitrogen. The acetyl peroxide solution was made by diluting 5.0 ml of a 25 per cent acetyl peroxide stock solution to 50.0 ml with benzene. The bottle was again flushed with nitrogen and capped. It was placed in a 73°C. bath for 3.5 hrs. and the reaction mixture was stirred with a magnetic bar. At the end of the reaction, 0.5 per cent of di-t-butylphenol was added. The polymer was filtered, washed with hexane and dried.

1.0 Gram of the dry "powdered" polymer was then suspended in 100 ml distilled water for 16 hours. The swelled polymer was filtered and weighed. The increase in weight of the polymer was recorded as the swellability of the polymer. The aqueous filtrate was evaporated to dryness with addition of a few ml is isopropanol. The residue left was recorded as solubles content (uncrosslinked) poly(ethylene oxide).

The swellability, solubles and insolubles (cross-linked poly(ethylene oxide)) of the polymer were 34.2, 23.4 and 76.6% respectively.

EXAMPLE 2

The same procedure of Example 1 was followed except that 0.3 g of neopentyl glycol diacrylate was used as the cross-linker and 1.2 ml of acetyl peroxide solution as initiator. The swellability, solubles and insolubles contents of the polymer were 36.0, 37.1% and 62.9% respectively.

EXAMPLE 3

The procedure described in Example 1 was followed except that 100 ml of hexane was used instead of the mixed solvent. The cross-linking agent added was 0.15 g (in 4 ml benzene) of polyethylene glycol (200) diacrylate and the acetyl peroxide solution used was 1.6 ml. The swellability, solubles and insolubles contents of the polymer were 16.8, 23.0% and 77% respectively.

EXAMPLE 4

The same procedures of Example 1 was used except that 100 ml of a silicone oil having the average formula $Me_3SiO(Me_2SiO)_xSiMe_3$ [wherein Me represents a methyl group]and having a viscosity of 30,000 centistokes at 25°C. was used as solvent and that the reaction mixture was kept 89°–90°C. for 20 minutes. The swellability, solubles and insolubles of the polymer were 17.0, 20.1% and 79.9% respectively.

EXAMPLE 5

The same procedure given in Example 1 was repeated except that the cross-linking agent used was 0.3 gram of 1,4-butylene glycol diacrylate and the acetyl peroxide solution used was 0.6 ml. The cross-linked product which was in the form of a free flowing powder, had a swellability of 26 and 88.3 per cent insoluble.

EXAMPLE 6

The same procedure given in Example 5 was used except that 0.12 gram of N,N-methylene bis-acrylamide was used instead of the 1,4-butylene glycol diacrylate. The swellability and insolubles of the polymer were 30.4 and 80.6 per cent respectively.

EXAMPLE 7

Into a pressure bottle, benzene (38 ml), hexane (50 ml), 7.5 g of poly(ethylene oxide) (molecular wt. ~4 × $10^6$), 0.23 g of soybean oil epoxide acrylate (in 4 ml benzene) and 1.0 ml of an acetyl peroxide solution were added after the bottle had been thoroughly flushed with $N_2$. The acetyl peroxide solution was made by diluting 5.0 ml of a 25 percent acetyl peroxide stock solution to 50.0 ml with benzene. The bottle was again flushed with $N_2$ and capped. It was placed in a 73°C. bath for 3.5 hours and the reaction mixture was stirred with a magnetic bar. At the end of the reaction, 0.05 percent of di-t-butylphenol was added. The polymer was filtered, washed with hexane and dried.

1.0 gram of the dry polymer was then suspended in 100 ml distilled water for 16 hours. The swelled polymer was filtered and weighed. The increase in weight of the polymer was recorded as the swellability of the polymer. The aqueous filtrate was evaporated to dryness with addition of a few ml of isopropanol. The residue left was recorded as solubles content (uncrosslinked poly(ethylene oxide)).

The swellability, solubles and insolubles (crosslinked poly(ethylene oxide)) of the polymer were 36.3, 24.5 and 75.5%, respectively.

EXAMPLE 8

The same procedure described in Example 7 was used except that 0.048 g of pentaerythritol triacrylate was added instead of soybean oil epoxide acrylate and 0.6 ml of acetyl peroxide solution was used. The swellability, solubles and insolubles of the polymer were 31.0, 22.8% and 77.2%, respectively.

EXAMPLE 9

The same procedure of Example 8 was used except that 0.24 gram of pentaerythritol triacrylate and 1.0 ml of acetyl peroxide solution were used. The swellability, solubles and insolubles of the polymer were 28.1, 18.6 and 81.4%, respectively.

EXAMPLE 10

The same procedure of Example 8 was used except that 0.024 gram of pentaerythritol triacrylate and 0.4 ml of acetyl peroxide solution were used. The swellability, solubles and insolubles of the polymer were 30.2, 31.9% and 6.81, respectively.

EXAMPLE 11

The same procedure of Example 7 was used escept that 0.17 gram of linseed oil epoxide acrylate was used instead of soybean oil epoxide acrylate and 0.6 ml of acetyl peroxide solution was used. The swellability, solubles and insolubles of the polymer were 34.6, 28.5% and 71.5%, respectively.

EXAMPLE 12

The same procedure of Example 11 was used except that 0.3 gram of linseed oil epoxide and 1.0 ml of acetyl peroxide solution were used. The swellability, solubles and insolubles of the polymer were 27.1, 17.7% and 82.3%, respectively.

EXAMPLE 13

Into a 2 l 4-necked round bottom flask, fitted with a mechanical stirrer, a condenser and an $N_2$ inlet and outlet tubing, hexane (1100 ml), 150 g of poly(ethylene oxide) (molecular weight ~4 × $10^6$), 0.6 g of pentaerythritol triacrylate and 1.18 g of lauroyl peroxide were added after the flask was well flushed with $N_2$. The reaction mixture was heated under $N_2$ at 73°C. for 3.5 hours. It was filtered and dried. The swellability, solubles and insolubles of the cross-linked product were 20.6, 26.6% and 73.4%, respectively.

EXAMPLE 14

The same method of Example 13 was used except that a mixture of benzene (450 ml) and hexane (600 ml) were used instead of hexane as reaction medium. The swellability, solubles and insolubles of the product were 27.4, 23.2% and 76.8%, respectively.

EXAMPLE 15

The same general procedure given in Example 7 was followed. Poly(ethylene oxide) (7.5 g molecular weight $5 \times 10^6$), benzene (38 ml), hexane (50 ml), soybean oil epoxide acrylate and 0.014 gram of 2,2'-azobis(2-methyl-propionitrile) were heated under nitrogen at 73°C for 2-3/4 hours. The polymer was filtered, washed with hexane and dried. The polymer had a swellability of 30 and 74.6 percent insolubles.

EXAMPLE 16

The same procedure described in Example 15 was followed except that 0.02 gram of benzoyl peroxide was used instead of the 2,2'-azobis(2-methylpropionitrile) and that the reaction was carried out at 73°C for 6.5 hours. The swellability of the polymer was 29 and the insolubles was 81.7 percent.

EXAMPLE 17

The same procedure given in Example 7 was used except that the cross-linking agent was 0.15 g of soybean oil epoxide acrylate and the acetyl peroxide solution used was 0.6 ml. The cross-linking reaction was carried out at 56°C for 24 hours. The swellability and the insolubles of the polymer were 31.3 and 81.7 percent.

The cross-linked poly(alkylene oxides) of this invention are of particular interest in agricultural applications and in providing water absorption articles or films. They can be used as plant growth media with soil, sand, peat moss and/or vermiculite. The growth media which comprise the cross-linked poly(alkylene oxides) and natural growth media, can also include active agents such as fertilizers, herbicides, fungicides and/or insecticides.

The cross-linked poly(alkylene oxides) of this invention are believed to be structurally a matrix of cross-linked poly(alkylene oxides) which are substantially insoluble in water, and organic solvents at ambient or elevated temperature; they will swell upon contact with liquids, solutions and/or suspensions into the polymeric matrix of the material; they will retain liquids and solutions incorporated into their matrix and will release the same to an environment which has a lower concentration of such liquids or solutions than that concentration of the liquid or solution within the polymeric matrix; they will incorporate liquids and solutions from the surrounding environment when the concentration of such liquids and solutions in the surrounding environment is greater than the concentration of the same within their polymeric matrix and the liquids and solutions are releasable from the polymeric matrix by evaporation.

Thus, the cross-linked poly(alkylene oxides) of the present invention are particularly suitable in those applications wherein a high degree of liquid absorbency is desired. Merely, as illustrative the cross-linked poly(alkylene oxides) of the present invention are particularly suitable as the absorbing media in baby diapers.

What is claimed is:

1. A process for producing powdered crosslinked poly (ethylene oxide) with a crosslinking agent represented by the formula

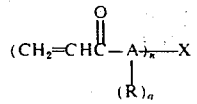

wherein A is nitrogen or oxygen; n has a value of 2 or more, R is hydrogen, an alkyl of 1–6 carbon atoms or aryl of 6 to 14 carbon atoms; X can be a (substituted or unsubstituted polyvalent) residue of an organic compound selected from the group consisting of — $C_yH_{2Y}$ — wherein Y is an integer of 1 to 50, — $C_xH_{2x}(OC_xH_{2x})m$ — wherein $x$ is an integer of 2 to 4 and $m$ is an integer of 1 to 1,000 or more, a polyvalent cycloalkyl of 5 to 7 ring carbon atoms, a polyvalent arylene of 6 to 14 ring carbon atoms,

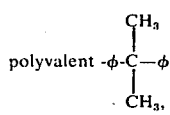

di or trivalent glyceryl, trimethylol propane, the divalent, trivalent and tetravalent residues of pentaerythritol, the polyvalent residues of the epoxidized fatty acid glycerides, and the divalent, trivalent or higher polyvalent residues of carbohydrates; with the proviso that when A is oxygen, $a$ is 0 and when A is nitrogen, $a$ is 1; in the presence of a free radical catalyst and a liquid medium containing a solvent-nonsolvent mixture for the poly(ethylene oxide) wherein the nonsolvent portion constitutes at least about 35% and up to 100% by weight of the liquid medium, at a temperature sufficiently elevated to effect cross-linking.

2. A process according to claim 1 wherein the cross-linking agent is pentaerythritol triacrylate.

3. A process according to claim 1 wherein said nonsolvent portion constitutes about 40% to about 80% by weight of said liquid medium.

4. A process according to claim 1 wherein the poly(alkylene oxide) is poly(ethylene oxide).

5. A process according to claim 1 wherein the solvent in said liquid mixture is benzene.

6. A process according to claim 1 wherein the nonsolvent in said liquid mixture is an aliphatic or cyclic hydrocarbon.

7. A process according to claim 1 wherein the free radical catalyst is an aliphatic diacylperoxide.

8. A process according to claim 1 wherein said poly(alkylene oxide) and cross-linking agent are contacted at temperatures within the range of about 50°C. to about 100°C.

9. A process according to claim 1 wherein said cross-linking agent is employed in an amount of about 2 to about 7 weight per cent based on the weight of the poly(alkylene oxide).

10. A process according to claim 1 wherein said liquid medium is employed on an amount of about 2 parts to about 40 parts liquid medium per part of poly(alkylene oxide).

11. A process according to claim 1 wherein the nonsolvent is present in the liquid medium in an amount of 100% by weight based on the weight of the liquid medium.

12. A process for producing powdered cross-linked poly(ethylene oxide) having a molecular weight of at least 100,000 which comprises contacting poly(ethylene oxide) with polyethylene glycol diacrylate as cross-linking agent in the presence of acetylperoxide as a free radical catalyst and a liquid medium containing about 40 to about 80% hexane and about 20 to 60% benzene at a temperature within the range of about 50°C. to about 100°C. for a time sufficient to cross-link said poly(ethylene oxide).

13. A process for producing powdered crosslinked poly(ethylene oxide) having a molecular weight of at least 100,000 which comprises contacting poly(ethylene oxide) with pentaerythritol triacrylate as cross-linking agent in the presence of an aliphatic diacylperioxide as a free radical catalyst and a liquid medium containing about 40 to about 80% hexane and about 20 to 60% benzene at a temperature within the range of about 50°C to about 100°C for a time sufficient to crosslink said poly(ethylene oxide).

14. A process according to claim 13 wherein said liquid medium is employed in an amount of about 2 parts to about 40 parts liquid medium per part of poly(ethylene oxide).

* * * * *

UNITED STATES PATENT OFFICE
CERTIFICATE OF CORRECTION

Patent No. 3,956,224      Issue Date May 11, 1976

Inventor(s) Nan S. Chu.

It is certified that error appears in the above-identified patent and that said Letters Patent are hereby corrected as shown below:

Column 9 -- lines 3 and 4 ----- delete "(substituted or unsubstituted polyvalent)"

Signed and Sealed this

Twelfth Day of October 1976

[SEAL]

Attest:

RUTH C. MASON
Attesting Officer

C. MARSHALL DANN
Commissioner of Patents and Trademarks